US00PP11897P2

(12) United States Plant Patent
van Rijn

(10) Patent No.: US PP11,897 P2
(45) Date of Patent: May 29, 2001

(54) ANTHURIUM PLANT NAMED 'RED FLARE'

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 09/484,663

(22) Filed: Jan. 18, 2000

(51) Int. Cl.[7] ..... A01H 5/00
(52) U.S. Cl. ..... Plt./365
(58) Field of Search ..... Plt./365, 369

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Anthurium plant named 'Red Flare', characterized by its upright and outwardly spreading plant habit; freely clumping growth habit; strong roots; large and durable dark green leaves that are elongated cordate in shape; spathes that are positioned upright and beyond the foliage on strong and erect scapes; large, durable, glossy bright red spathes; year-round continuous flowering; good flowering performance under low light condition; resistance to Xanthomonas and Colletotrichum; tolerance to low and high temperatures; and good post-production longevity.

2 Drawing Sheets

BACKGROUND OF THE INVENTION

The present invention relates to a new and distinct cultivar of Anthurium plant, botanically known as *Anthurium andreanum*, and hereinafter referred to by the cultivar name 'Red Flare'.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor of the Inventor's proprietary *Anthurium andreanum* selection code number 90-6 as the female, or seed, parent with the Inventor's proprietary *Anthurium andreanum* selection code number 90-3 as the male, or pollen, parent. The cultivar 'Red Flare' was discovered and selected by the Inventor as a plant within the progeny of the stated cross in a controlled environment in Schipluiden, The Netherlands, on Nov. 5, 1991.

Asexual propagation of the new cultivar by tissue culture has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Red Flare'. These characteristics in combination distinguish 'Red Flare' as a new and distinct cultivar:

1. Upright and outwardly spreading plant habit.
2. Freely clumping growth habit.
3. Strong roots.

4. Large and durable dark green leaves that are elongated cordate in shape. Dark green color is maintained under conditions of high light.
5. Spathes that are positioned upright and beyond the foliage on strong and erect scapes.
6. Large, durable, glossy bright red spathes.
7. Year-round continuous flowering.
8. Good flowering performance under low light conditions.
9. Resistant to Xanthomonas and Colletotrichum.
10. Tolerant to low and high temperatures.
11. Good post-production longevity.

The new Anthurium can be compared to the female parent, the Inventor's proprietary selection code number 90-6, described as having pink-colored spathes. In side-by-side comparisons conducted by the Inventor in Schipluiden, The Netherlands, plants of the new Anthurium differ from plants of selection code number 90-6 in the following characteristics:

1. Plants of the new Anthurium are more compact than plants of the selection code number 90-6.
2. Plants of the new Anthurium have darker green, narrower and more durable leaves than plants of the selection code number 90-6.
3. Plants of the new Anthurium have smaller spathes than plants of the selection code number 90-6.

The new Anthurium can be compared to the male parent, the Inventor's proprietary selection code number 90-3. In side-by-side comparisons conducted by the Inventor in Schipluiden, The Netherlands, plants of the new Anthurium differ from plants of selection code number 90-3 in the following characteristics:

1. Plants of the new Anthurium are not as compact as plants of the selection code number 90-3.
2. Plants of the new Anthurium have larger, darker green and more durable leaves than plants of the selection code number 90-3.
3. Plants of the new Anthurium have larger spathes than plants of the selection code number 90-3.

The new Anthurium can be compared to the Anthurium cultivar 'Lady Jane', not patented. In side-by-side comparisons conducted by the Inventor in Schipluiden, The Netherlands, plants of the new Anthurium differ from plants of the cultivar 'Lady Jane' in the following characteristics:

1. Plants of the new Anthurium have darker green and more durable leaves than plants of the cultivar 'Lady Jane'.
2. Plants of the new Anthurium have larger spathes than plants of the cultivar 'Lady Jane'.
3. Plants of the new Anthurium and the cultivar 'Lady Jane' differ in spathe coloration as plants of the cultivar 'Lady Jane' have pink-colored spathes.
4. Plants of the new Anthurium are more resistant to pathogens common to Anthuriums than plants of the cultivar 'Lady Jane'.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the actual colors of the new Anthurium.

The photograph in the first sheet comprises a side perspective view of a typical potted plant of the cultivar 'Red Flare'. The photograph at the top of the second sheet comprises a close-up view of a typical inflorescence of the cultivar 'Red Flare'.

The photograph at the bottom of the second sheet comprises a close-up view of typical mature (left and young (right) leaves of the cultivar 'Red Flare'.

DETAILED BOTANICAL DESCRIPTION

In the following description, color references are made to The Royal Horticultural Society Colour Chart except where general terms of ordinary dictionary significance are used. The following observations and measurements describe rooted liners that were grown for about 8 months in 20-cm containers in Sebring, Fla., under conditions which closely approximate commercial production conditions.

Botanical classification: *Anthurium andreanum* cultivar 'Red Flare'.

Parentage:

*Female parent.*—Inventor's proprietary *Anthurium andreanum* selection identified as code number 90-6, not patented.

*Male parent.*—Inventor's proprietarty *Anthurium andreanum* selection identified as code number 90-3, not patented.

Propagation:

*Method.*—Typically by tissue culture.

*Time to root tissue-cultured liners.*—About 12 to 16 weeks.

*Root description.*—Strong fleshy roots.

Plant description:

*Plant shape.*—Upright and outwardly spreading, inverted triangle, symmetrical.

*Growth habit.*—Freely clumping, bushy and dense. Appropriate for 15 to 40-cm containers.

*Crop time.*—From rooted liners, about 8 to 9 months are required to produce finished flowering plants in 15-cm containers.

*Plant height.*—About 45 cm from soil level to leaf plane.

*Plant width.*—About 62 cm.

*Plant vigor.*—High.

*Growth rate.*—*Moderate.*

*Foliage description.*—Length: About 28 cm. Width: About 17 cm. Shape: Elongated cordate. Apex: Accuminate. Base: Strongly cordate; lobes not overlapping. Margin: Entire. Texture: Smooth, glabrous; leathery, flexible, durable. Color: Young leaves, upper surface: Greener than 146A; very glossy. Young leaves, lower surface: Close to 146B. Mature leaves, upper surface: Much darker than 147A; glossy. Mature leaves, lower surface: Greener than 146A. Venation, upper surface: 144A. Venation, lower surface: 144B. Petiole: Length: About 42 cm. Diameter, at base: About 7.5 mm. Shape: Cylindrical. Color: 144A to 146A; occasionally faint anthocyanin, close to 178A, overtones; anthocyanin most prominent at the geniculum and above to the leaf base. Genticulum position: About 3.5 cm below leaf. Geniculum length: About 1.2 cm. Geniculum diameter: About 6 mm. Geniculum color: 144A with anthocyanin, close to 178A, overtones.

Inflorescence description:

*Inflorescence arrangement.*—Spathes with spadices held beyond the foliage. Flowering structures arise from leaf axils. Freely flowering; continuous flowering year-round; numerous spathes/spadices per plant about five per plant. Not fragrant.

*Inflorescence longevity.*—Spathes/spadices last about three months under summer conditions; persistent.

*Flowers.*—Quantity per spadix: Numerous, typically more than 200. Shape: Rounded. Diameter: About 1.5 mm.

*Spathe.*—Length: About 9 cm. Width: About 8 cm. Shape: Cordate. Apex: Acuminate, elongated. Base: Auriculate to cordate, lobes not overlapping. Margin: Entire. Texture: Leathery, glabrous, glossy. Color: When opening: Close to 45A. Front surface: 45C to 45D. Back surface: 45A fading to 52A. After senescence: 51A to 52B to 52C.

*Spadix.*—Length: About 8.5 cm. Diameter: Apex: About 3 mm. Base: About 7 mm. Shape: Columnar. Cross section: Rounded. Color: Young: 15A. Mature: Initially yellow, 15A; becoming light pale yellow, 4D; after senescence, green, 144A.

*Scape.*—Length: About 42 cm. Diameter, base: About 5 mm. Aspect: Strong and erect; flexible. Color: 144A with anthocyanin, close to 178A, overtones.

*Reproductive organs.*—Androecium: Pollen color: Creamy white, 158D. Gynoecium: Stigma shape: Ovoid.

*Seed.*—Seed development on plants of the new Anthurium has not been observed.

Disease resistance: In outdoor field trials, plants of the new Anthurium have exhibited resistance to Xanthomonas and Colletotrichum.

Temperature tolerance: Plants of the new Anthurium are tolerant to low temperatures to about 10° C. and to high temperatures greater than 38° C.

It is claimed:

1. A new and distinct cultivar of Anthurium plant named 'Red Flare', as illustrated and described.

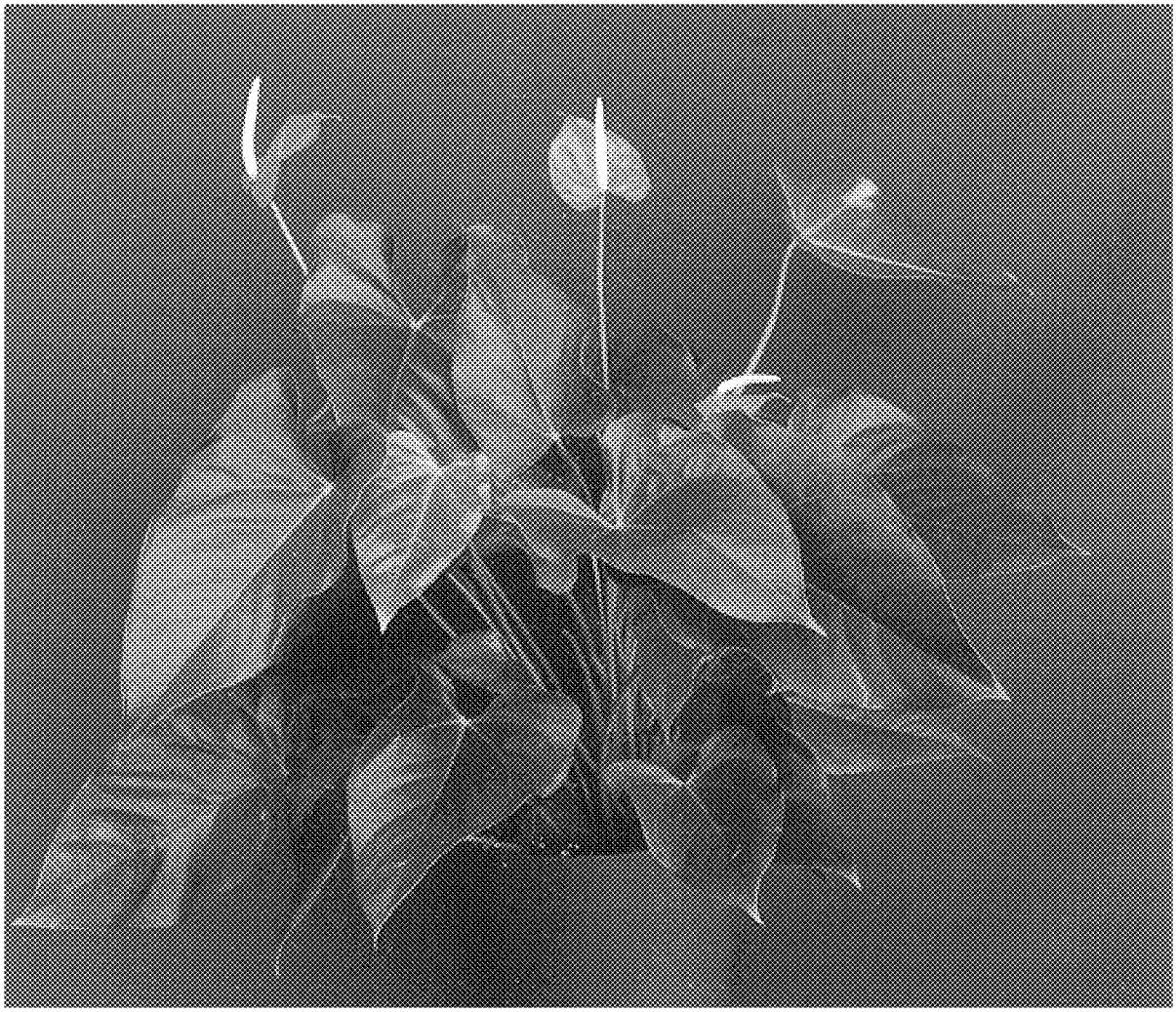

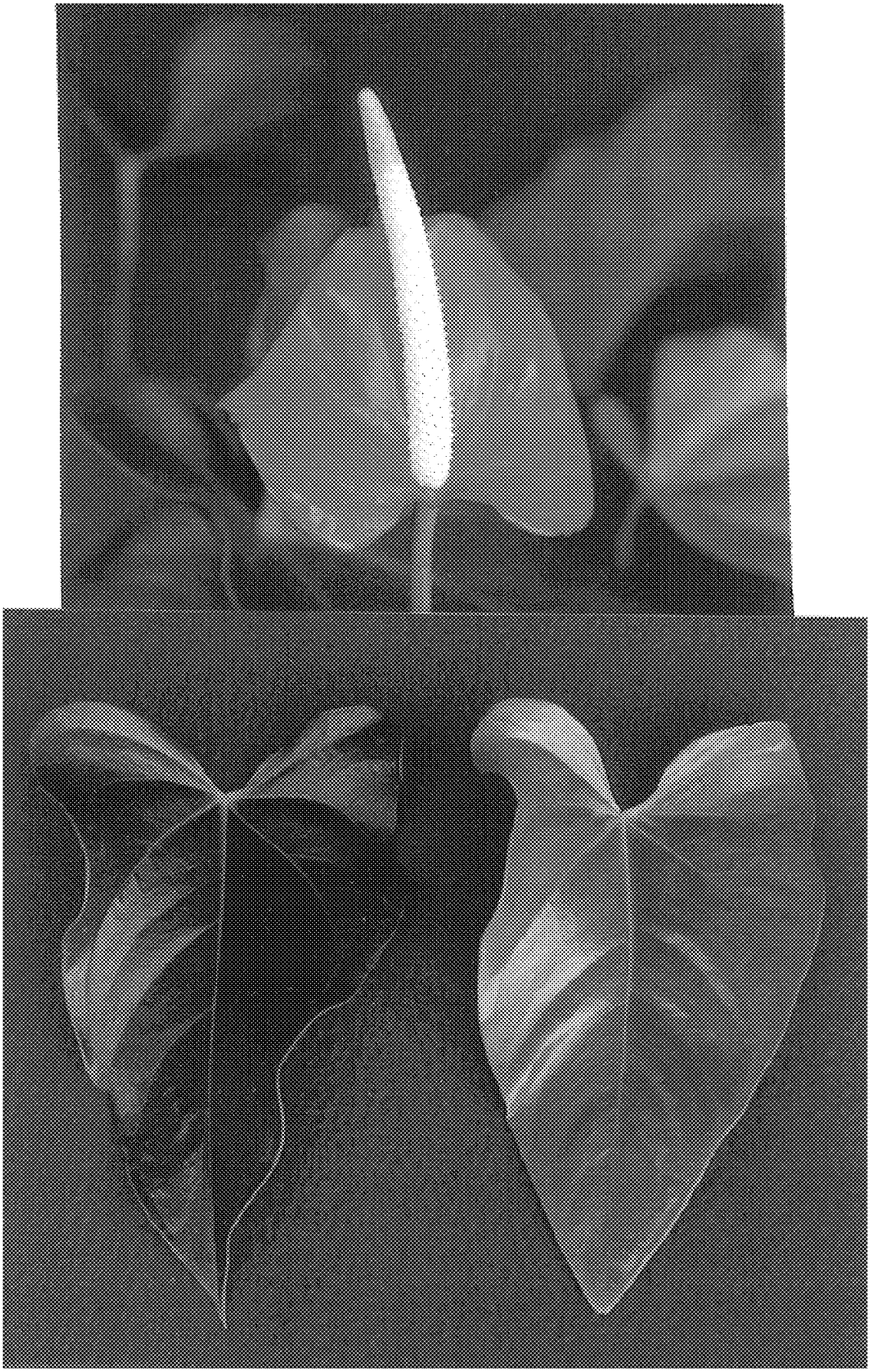

* * * * *